(12) United States Patent
Feng et al.

(10) Patent No.: US 11,299,474 B2
(45) Date of Patent: Apr. 12, 2022

(54) CRYSTAL FORM TARGETING CDK4/6 KINASE INHIBITOR

(71) Applicant: XUANZHU BIOPHARMACEUTICAL CO., LTD., Shijiazhuang (CN)

(72) Inventors: Yuzhen Feng, Jinan (CN); Lan Fang, Jinan (CN)

(73) Assignee: XUANZHU BIOPHARMACEUTICAL CO., LTD., Shijiazhuang (CN)

( * ) Notice: Subject to any disclaimer, the term of this patent is extended or adjusted under 35 U.S.C. 154(b) by 0 days.

(21) Appl. No.: 16/965,503

(22) PCT Filed: Dec. 27, 2018

(86) PCT No.: PCT/CN2018/124418
§ 371 (c)(1),
(2) Date: Jul. 28, 2020

(87) PCT Pub. No.: WO2019/144759
PCT Pub. Date: Aug. 1, 2019

(65) Prior Publication Data
US 2021/0047292 A1 Feb. 18, 2021

(30) Foreign Application Priority Data
Jan. 29, 2018 (CN) .......................... 201810084351.3

(51) Int. Cl.
*C07D 401/14* (2006.01)
*A61K 45/06* (2006.01)

(52) U.S. Cl.
CPC ............ *C07D 401/14* (2013.01); *A61K 45/06* (2013.01); *C07B 2200/13* (2013.01)

(58) Field of Classification Search
None
See application file for complete search history.

(56) References Cited

U.S. PATENT DOCUMENTS 9,796,701 B2 * 10/2017 Wu ...................... C07D 401/04

FOREIGN PATENT DOCUMENTS

| WO | 2010125004 A1 | 11/2010 |
| WO | 2015101293 A1 | 7/2015 |
| WO | 2016169422 A1 | 10/2016 |

OTHER PUBLICATIONS

Goel, et al., Trends in Cell Biology (2018), 28(11), pp. 911-925.*
International Search Report and Written Opinion for PCT/CN2018/124418, filed Dec. 27, 2018, dated Feb. 21, 2019.

* cited by examiner

*Primary Examiner* — Brian J Davis
(74) *Attorney, Agent, or Firm* — Fox Rothschild LLP

(57) ABSTRACT

The present disclosure relates to crystal form A of 5-((4-ethylpiperazin-1-yl)methyl)-N-(5-fluoro-4-(4-fluoro-1-isopropyl-2-methyl-1H-benzo[d]imidazol-6-yl)pyridin-2-yl)pyrimidin-2-amine. The crystal form has a high purity, less residual solvent, high solubility and good stability; has good properties, fluidity and compressibility, and is convenient for production, detection, preparation of formulations, transportation and storage. The preparation method is easy to operate and is suitable for industrial production, and the crystal form can be used for treating and/or preventing diseases associated with CDK4/6 kinase-mediated cancers.

20 Claims, 2 Drawing Sheets

Temperature (°C)

CRYSTAL FORM TARGETING CDK4/6 KINASE INHIBITOR

This application is a U.S. national phase application of International Application No. PCT/CN2018/124418, filed on Dec. 27, 2018, which claims the benefits of Chinese Patent Application No. 201810084351.3 filed on Jan. 29, 2018, the disclosures of which are hereby incorporated by reference in their entirety for all purpose.

TECHNICAL FIELD

The present disclosure relates to a crystal form of an inhibitor targeting CDK4/6 kinase and a preparation method thereof, and also relates to a pharmaceutical composition containing the crystal form, and the use of such a compound for reducing or inhibiting the activity of the CDK4/6 kinase in cells and for treating and/or preventing diseases associated with CDK4/6 kinase-mediated cancers.

BACKGROUND ART

The chemical name of a compound of formula (I) is 5-((4-ethylpiperazin-1-yl)methyl)-N-(5-fluoro-4-(4-fluoro-1-isopropyl-2-methyl-1H-benzo[d]imidazol-6-yl)pyridin-2-yl)pyrimidin-2-amine (hereinafter referred to as "compound of formula (I)", which has been described in the patent application PCT/CN 2014/095615), which acts as an inhibitor that targets the cyclin-dependent kinase 4/6 (CDK4/6) kinase. Studies have shown that among CDK isoforms involved in the cell cycle, CDK4/6 plays an irreplaceable role. Cancer-associated cell cycle mutations are mainly present in the G1 phase and G1/S phase transition process. A complex formed from CDK4/6 and Cyclin D results in the phosphorylation of the antioncogene Rb to form pRb and the release of the bound transcriptional factor E2F, causing the transcription of genes associated with S phase initiation, thereby promoting cells to pass a checkpoint and to transit from G1 phase to S phase. About 80% of human tumors have abnormalities in the cyclin D-CDK4/6-INK4-Rb pathway. The alteration of this pathway results in accelerated G1 phase so that tumor cells proliferate in an accelerated manner and thus acquire survival advantages. Therefore, intervention in this pathway has become a strategy of treatment, and CDK4/6 has become a new anti-tumor target. CDK4/6 has advantages as an anti-tumor target in the following two aspects: (1) the proliferation of most proliferative cells is dependent on CDK2 or CDK4/6; however, CDK4/6 inhibitors do not exhibit the cytotoxicity of "pan-CDK inhibitors", such as bone marrow depression and intestinal reactions. (2) Preclinical experiments have shown that if the level of cyclin D is increased or P16INK4a is inactivated in cells, the sensitivity of the cells to drugs can be increased, and since tumor cells have the above-mentioned phenomena relative to normal cells, the targeting ability of drugs is increased to some extent.

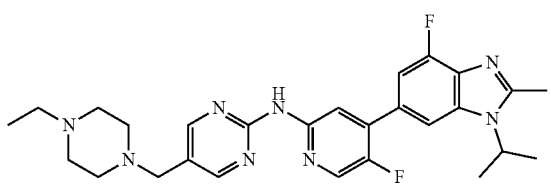

Formula (I)

The study of crystal forms plays an important role in the process of drug development, and there are significant differences in solubility, stability, bioavailability, etc. among different crystal forms of the same drug. In order to better control the quality of a drug to meet the requirements of formulation preparation, production, transportation, storage, etc., we have studied the crystal form of the compound of formula (I) to discover crystal forms with good properties.

SUMMARY OF THE INVENTION

The present disclosure relates to crystal form A of 5-((4-ethylpiperazin-1-yl)methyl)-N-(5-fluoro-4-(4-fluoro-1-iso-propyl-2-methyl-1H-benzo[d]imidazol-6-yl)pyridin-2-yl)pyrimidin-2-amine represented by formula (I) as a targeting CDK4/6 kinase inhibitor. The present disclosure also relates to a method for preparing the crystal form A, a pharmaceutical composition containing the crystal form A, and the use of such a compound for reducing or inhibiting the activity of the CDK4/6 kinase in cells and for treating and/or preventing diseases associated with CDK4/6 kinase-mediated cancers.

In certain embodiments, the present disclosure provides crystal form A of the compound of formula (I),

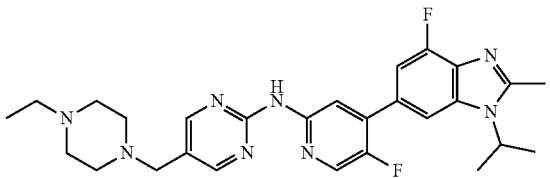

Formula (I)

wherein the crystal form A of the compound of formula (I) is characterized by an X-ray powder diffraction pattern comprising characteristic peaks at 6.6±0.2°, 10.0±0.2°, 13.2±0.2°, 17.4±0.2°, 20.1±0.2°, and 20.6±0.2° expressed by 2θ angle (°) using Cu-Kα radiation.

In certain embodiments, the crystal form A of the compound of formula (I) further has characteristic peaks at 8.7±0.2°, 10.9±0.2°, 15.7±0.2°, 16.4±0.2°, and 30.4±0.2° in addition to the above-mentioned characteristic peaks.

In certain embodiments, the crystal form A of the compound of formula (I) further has characteristic peaks at 16.7±0.2°, 19.3±0.2°, 22.2±0.2°, 23.3±0.2°, 24.0±0.2°, 25.9±0.2°, and 28.1±0.2° in addition to the above-mentioned characteristic peaks.

In certain embodiments, the crystal form A of the compound of formula (I) is characterized by an X-ray powder diffraction pattern comprising characteristic peaks at 6.6±0.2°, 8.7±0.2°, 10.0±0.2°, 10.9±0.2°, 13.2±0.2°, 15.7±0.2°, 16.4±0.2°, 17.4±0.2°, 20.1±0.2°, 20.6±0.2°, and 30.4±0.2° expressed as 2θ angles using Cu-Kα radiation.

In certain embodiments, the crystal form A of the compound of formula (I) is characterized by an X-ray powder diffraction pattern comprising characteristic peaks at 6.6±0.2°, 8.7±0.2°, 10.0±0.2°, 10.9±0.2°, 13.2±0.2°, 15.7±0.2°, 16.4±0.2°, 16.7±0.2°, 17.4±0.2°, 19.3±0.2°, 20.1±0.2°, 20.6±0.2°, 22.2±0.2°, 23.3±0.2°, 24.0±0.2°, 25.9±0.2°, 28.1±0.2°, and 30.4±0.2° expressed as 2θ angles using Cu-Kα radiation.

In certain embodiments, the crystal form A of the compound of formula (I) has an X-ray powder diffraction pattern obtained using Cu-Kα radiation substantially as shown in FIG. 1.

In certain embodiments, the crystal form A of the compound of formula (I) is characterized by a differential scanning calorimetry (DSC) diagram comprising an endothermic peak at about 195-215° C.

In certain embodiments, the crystal form A of the compound of formula (I) is characterized by a differential scanning calorimetry (DSC) diagram comprising an endothermic peak at 205±3° C.

In certain embodiments, the crystal form A of the compound of formula (I) is characterized by a differential scanning calorimetry (DSC) diagram substantially as shown in FIG. 2.

In certain embodiments, the crystal form A of the compound of formula (I) is characterized by having an X-ray powder diffraction pattern, substantially as shown in FIG. 1.

In certain embodiments, the crystal form A of the compound of formula (I) is characterized by a differential scanning calorimetry diagram comprising an endothermic peak within a range of about 195° C. to 215° C., preferably within a range of 205±3° C., and more preferably by a differential scanning calorimetry diagram substantially as shown in FIG. 2.

In certain embodiments, the crystal form A of the compound of formula (I) is characterized by having a TGA diagram in which there is no obvious weight loss within a range of 0° C.-250° C., preferably by having a thermogravimetric analysis diagram substantially as shown in FIG. 2.

In certain embodiments, the crystal form A of the compound of formula (I) is characterized by having a $^1$H-NMR spectrum substantially as shown in FIG. 3.

In certain embodiments, the crystal form A of the compound of formula (I) is characterized in that the crystal structure thereof is in a substantially pure form.

In certain embodiments, the present disclosure also provides a method for preparing the crystal form A of the compound of formula (I), the method comprising:

dissolving the compound of formula (I) in an organic solvent, then stirring, and collecting a precipitated solid.

In certain embodiments, the method for preparing the crystal form A of the compound of formula (I) comprises:

dissolving the compound of formula (I) in an organic solvent, and heating the same to 60-100° C. with stirring until the compound is dissolved;

cooling to 0-25° C., and stirring at a constant temperature for 1-24 h; and collecting a precipitated solid.

In certain embodiments, the method for preparing the crystal form A of the compound of formula (I) comprises:

dissolving the compound of formula (I) in an organic solvent, and heating the same to 60-100° C. with stirring until the compound is dissolved;

cooling to 30-55° C. to precipitate out a solid;

cooling to 0-25° C., and stirring at a constant temperature for 1-24 h; and collecting a precipitated solid, and drying.

In certain embodiments, the method for preparing the crystal form A of the compound of formula (I) comprises dissolving the compound of formula (I) in an organic solvent, heating the same to 60-100° C. and stirring until the compound is dissolved, cooling to 0-25° C. with stirring to precipitate out a solid, keeping at a constant temperature, stirring for 1-24 h, filtering with suction, and drying to obtain the crystal form A.

In certain embodiments, the method for preparing the crystal form A of the compound of formula (I) comprises:

dissolving the compound of formula (I) in an organic solvent, and heating the same to 70-100° C.;

after the compound is dissolved, cooling to 50-75° C., adding a seed crystal, and keeping at a constant temperature to precipitate out a solid; and slowly cooling to 0-25° C., keeping at a constant temperature, collecting a precipitated solid, and drying to obtain the crystal form A.

In certain embodiments, the seed crystal is the crystal form A of the compound of formula (I) or the solid precipitated during the preparation of the crystal form A of the compound of formula (I).

In certain embodiments, the amount of the seed crystal added is 0.1%-3%, e.g. 0.1%-0.2%, 0.2%-0.5%, 0.5%-1%, 1%-1.5%, 1.5%-2%, 2%-2.5% or 2.5%-3%, of the mass of the compound of formula (I).

In certain embodiments, the method for preparing the crystal form A of the compound of formula (I) comprises dissolving the compound of formula (I) in an organic solvent, and heating the same to 70-100° C.; after the compound is dissolved and cooled to 50-65° C., optionally adding a certain amount of seed crystal, and keeping at a constant temperature; when a solid appears, slowly cooling to 0-25° C., and keeping at a constant temperature; and filtering with suction, and drying to obtain the crystal form A. The seed crystal is selected from the crystal form A or the solid precipitated out before drying during the preparation of the crystal form A, and the crystal form A can be prepared by another crystal form A preparation method in which no seed crystal is added, as described in the present disclosure. The ratio of the mass of the seed crystal to the mass of the compound of formula (I) is 0.1%-3%, preferably 0.1%-0.2%, 0.2%-0.5%, 0.5%-1%, 1%-1.5%, 1.5%-2%, 2%-2.5%, or 2.5%-3%.

In certain embodiments, the method for preparing the crystal form A of the compound of formula (I) comprises:

dissolving the compound of formula (I) in an organic solvent, and heating the same to 70-100° C.; after the compound is dissolved and cooled to 50-65° C., adding a seed crystal, and keeping at a constant temperature; when a solid appears, slowly cooling to 0-25° C., and keeping at a constant temperature; filtering with suction, and drying to obtain the crystal form A, wherein the seed crystal is selected from the crystal form A or a solid before drying during the preparation of the crystal form A, and the mass ratio of the seed crystal and the compound of formula (I) is 0.1%-3%, preferably 0.1%-0.2%, 0.2%-0.5%, 0.5%-1%, 1%-1.5%, 1.5%-2%, 2%-2.5%, or 2.5%-3%.

In certain embodiments, the method for preparing the seed crystal comprises dissolving the compound of formula (I) in an organic solvent, heating the same to 60-100° C. and stirring until the compound is dissolved, keeping at a constant temperature, reducing the stirring speed, cooling to 50-65° C., increasing the stirring speed, slowly cooling to 0-25° C. to precipitate out a solid, keeping at a constant temperature, stirring for 1-24 h, and filtering with suction to obtain the seed crystal.

In certain embodiments, in the preparation methods for the crystal form A and the seed crystal, the heating temperature is 60-100° C., preferably 70-100° C., preferably 80-100° C., preferably 90-100° C., and a preferred heating temperature is the temperature at which the sample dissolves and becomes clear.

In certain embodiments, in the preparation methods for the crystal form A and the seed crystal, the temperature is reduced to 0-25° C., preferably 5-10° C., preferably 5-20° C., preferably 10-15° C., preferably 15-25° C., and during the cooling, the cooling can be optionally carried out multiple times through different temperatures. The rate of cooling is preferably 3-15° C./h, preferably 5-10° C./h, preferably 6° C./h, preferably 9° C./h; and cooling methods include but are not limited to natural cooling, ice bath cooling, oil bath cooling, cooling by using refrigeration equipment, etc., wherein the natural cooling, oil bath cooling, and cooling by using refrigeration equipment are preferred in the present disclosure.

In certain embodiments, with regard to the stirring in the preparation methods for the crystal form A and the seed crystal, stirring methods thereof include but are not limited to mechanical stirring, magnetic stirring, etc.; and the stirring speed thereof is preferably 500-100 r/min, preferably 300 r/min, or 150 r/min (the rotation speed can be adjusted according to the size of a stirring paddle. If the size of the stirring paddle is relatively large, the rotation speed can be appropriately reduced), and the stirring time thereof is preferably 0.5-10 h, preferably 0.5-1 h, preferably 1-6 h, preferably 1.5-5 h.

In certain embodiments, in the preparation methods for the crystal form A and the seed crystal, the compound of formula (I) is dissolved in an organic solvent selected from one of or any combination of two or more of the following solvents:

(1) alcohol solvents selected from fatty alcohol solvents, alicyclic alcohol solvents and aromatic alcohol solvents, wherein the fatty alcohol solvents are selected from methanol, ethanol, propanol, isopropanol, n-butanol, isobutanol, tert-butanol, sec-butanol, n-pentanol, n-hexanol, ethylene glycol, propylene glycol or glycerol; the alicyclic alcohol solvents are selected from cyclopentanol, cyclopentylmethanol, cyclohexanol, cyclohexylmethanol or cyclohexylethanol; and the aromatic alcohol solvents are selected from benzyl alcohol, phenylethanol or phenylpropanol;

(2) ketone solvents selected from fatty ketone solvents and cyclic ketone solvents, wherein the fatty ketone solvents are selected from methyl ethyl ketone, methyl isopropyl ketone, acetone, methyl butanone or methyl isobutyl ketone; and the cyclic ketone solvents are selected from cyclopropanone, cyclohexanone, isophorone or N-methylpyrrolidone;

(3) nitrile solvents selected from acetonitrile or propionitrile;

(4) ether solvents selected from fatty ether solvents and cyclic ether solvents, wherein the fatty ether solvents are selected from diethyl ether, dipropyl ether, diisopropyl ether, methyl tert-butyl ether, ethyl butyl ether, ethyl tert-butyl ether, dibutyl ether or dipentyl ether, and the cyclic ether solvents are selected from ethylene oxide, 1,2-propylene oxide, tetrahydrofuran, 2-methylfuran, dioxolane or 1,4-dioxane;

(5) amide solvents selected from formamide, N,N-dimethylformamide, N,N-dimethylacetamide, N,N-dimethylpropionamide or N,N-diethylpropionamide; and (6) sulfoxide solvents selected from dimethyl sulfoxide, diethyl sulfoxide or benzyl phenyl sulfoxide, The alcohol, ketone, nitrile, ether, amide, and sulfoxide solvents as noted above are not limited to the specific examples listed, and any solvents belonging to the above categories can achieve the functions of the present disclosure, i.e. preparing the crystal form A of the compound of formula (I).

With regard to the organic solvents, the "any combination of two or more solvents" refers to a solvent formed by mixing organic solvents in the same category or different categories from the above-mentioned organic solvents at a certain ratio. Mixed solvents formed from solvents in the same category include but are not limited to the following specific examples: methanol/ethanol, methanol/isopropanol, methanol/ethanol/isopropanol, methanol/tert-butanol, methanol/cyclopentanol, methanol/benzyl alcohol, ethanol/isopropanol, ethanol/tert-butanol, diethyl ether/tetrahydrofuran, etc. The mixed solvents formed from solvents in different categories include but are not limited to the following mixed solvent systems: alcohols/ketones, alcohols/ethers, alcohols/amides, ketones/amides, etc.

In certain embodiments, the organic solvent is an alcohol solvent or a ketone solvent.

In certain embodiments, the organic solvent is selected from acetone, isopropanol, butanol and n-pentanol.

In certain embodiments, in the preparation methods for the crystal form A and the seed crystal, the drying methods include but are not limited to natural airing at room temperature, infrared lamp drying, oven drying, dryer drying, and preferably drying under vacuum conditions; a preferred drying temperature is 30-100° C., preferably 30-80° C., preferably 35-70° C., preferably 40-65° C., preferably 35-55° C.; during the drying process, drying can optionally be carried out multiple times at different temperatures; and preferred drying times are 5-48 h, 10-36 h, and 15-24 h.

In certain embodiments, the present disclosure also provides a pharmaceutical composition containing the crystal form A of the compound of formula (I) of the present disclosure, and optionally one or more pharmaceutical carriers and/or diluents. In certain embodiments, the pharmaceutical composition of the present disclosure may be in any pharmaceutically acceptable dosage form, such as a solution, tablets, capsules, or an injection, and such a pharmaceutical composition may be administered by an injection route or by oral administration. In certain embodiments, the crystal form A of the compound of formula (I) of the present disclosure or the pharmaceutical composition thereof is preferably orally administered.

In certain embodiments, the pharmaceutical composition containing the crystal form (e.g. crystal form A) of the compound of formula (I) and optionally one or more pharmaceutical carriers and/or diluents, as described in the present disclosure, may be in any pharmaceutically acceptable dosage form. It is administered to a patient in need thereof orally, parenterally, rectally, transpulmonarily, etc. For oral administration, it may be prepared into conventional solid formulations, such as tablets, capsules, pills, granules, etc., or may also be prepared into oral liquid formulations, such as oral solutions, oral suspensions, syrups, etc. In the case of preparing an oral preparation, a suitable filler, binder, disintegrant, lubricant, etc. may be added. When used for parenteral administration, it can be prepared into injections, including injectable solutions, sterile powders for injection, and concentrated solutions for injection. In the case of preparing an injection, it can be produced by using a conventional method in the existing pharmaceutical field, and in the case of preparing an injection, no additives may be added, or appropriate additives may be added according to the nature of the drug. When used for rectal administration, it can be prepared into a suppository, etc. When used for pulmonary administration, it can be prepared into an inhalant, a spray, etc.

In certain embodiments, the pharmaceutical composition of the present disclosure may further comprise one or more additional anti-tumor agents and/or immunosuppressive agents. The additional anti-tumor agents and/or immunosuppressive agents are selected from one or more of methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecin, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, nitrogen mustard, melphalan, chlorambucil, carboplatin, cisplatin, oxaliplatin, lobaplatin, topotecan, camptothecin, hycamtin, everolimus, sirolimus, temsirolimus, 6-mercaptopurine, 6-thioguanine, azathioprine, mycin D, daunorubicin, amycin, mitoxantrone, blenoxane, plicamycin, and aminoglutethimide.

In certain embodiments, the present disclosure also provides the use of the crystal form (e.g. crystal form A) of the compound of formula (I) of the present disclosure or the pharmaceutical composition of the present disclosure in the preparation of a medicament for treating and/or preventing diseases associated with CDK4/6 kinase-mediated cancers in a subject.

In certain embodiments, the present disclosure also provides a method for treating and/or preventing diseases associated with CDK4/6 kinase-mediated cancers in a mammal in need thereof, the method comprising administering to the mammal in need thereof a therapeutically and/or prophylactically effective amount of the crystal form A of the compound of formula (I) or the pharmaceutical composition of the present disclosure.

In certain embodiments, the present disclosure also provides the crystal form A of the compound of formula (I), for use in a medicament for treating and/or preventing diseases associated with CDK4/6 kinase-mediated cancers.

In the present disclosure, the diseases associated with CDK4/6 kinase-mediated cancers is selected from brain tumor, lung cancer, squamous cell carcinoma, bladder cancer, stomach cancer, ovarian cancer, peritoneal cancer, pancreatic cancer, breast cancer, head and neck cancer, cervical cancer, endometrial cancer, rectal cancer, liver cancer, kidney cancer, esophageal adenocarcinoma, esophageal squamous cell carcinoma, prostatic cancer, female reproductive tract cancer, carcinoma in situ, lymphoma, neurofibromatosis, thyroid cancer, bone cancer, skin cancer, brain cancer, colon cancer, testicular cancer, gastrointestinal stromal tumor, prostate tumor, mast cell tumor, multiple myeloma, melanoma, glioma, and sarcoma.

The term "about" as used in the present disclosure, for example, when used for modifying a certain numerical value or numerical range, refers to including the numerical value or numerical range, and an error range acceptable to a person skilled in the art with regard to the numerical value or numerical range, for example, the error range is ±10%, ±5%, ±4%, ±3%, ±2%, ±1%, ±0.5%, etc.

The actual dosage level of each active ingredient in the pharmaceutical composition of the present disclosure can be varied so that the resulting amount of the active compound can be effective to achieve a desired therapeutic response for a specific patient, composition and mode of administration. The dosage level should be selected based on the activity of the specific compound or crystal form thereof, the route of administration, the severity of the condition being treated, and the condition and past medical history of the patient to be treated. However, it is the practice in the art that the dosage of the compound or crystal form thereof is started at a level lower than that required to obtain a desired therapeutic effect, and the dosage is gradually increased until the desired effect is achieved.

When used in the above-mentioned treatment and/or prevention or other treatments and/or preventions, a therapeutically and/or prophylactically effective amount of the crystal form A of the compound of formula (I) of the present disclosure can be applied in pure form. Alternatively, the crystal form A of the compound of formula (I) may be administered in a pharmaceutical composition containing the crystal form A of the compound of formula (I) and one or more pharmaceutically acceptable excipients. The phrase "therapeutically and/or prophylactically effective amount" of the crystal form A of the compound of formula (I) of the present disclosure refers to an amount of the compound that is sufficient to treat a disorder with a rational effect/risk ratio applicable to any medical treatment and/or prevention. However, it should be recognized that the total daily dosage of the crystal form A of the compound of formula (I) and the pharmaceutical composition, as described in the present disclosure, should be determined by the attending physician within the scope of reliable medical judgment. For any particular patient, the specific therapeutically effective dosage level should depend on a variety of factors, including the disorder being treated and the severity of the disorder; the activity of the specific compound used or the crystal form thereof; the specific composition used; the age, body weight, general health status, gender, and diet of the patient; the administration time, administration route, and excretion rate of the specific compound used or the crystal form thereof; the duration of the treatment; the drug used in combination or simultaneously with the specific compound used or the crystal form thereof; and similar factors well known in the medical field. For example, it is the practice in the art that the dosage of the compound or crystal form thereof is started at a level lower than that required to obtain a desired therapeutic effect, and the dosage is gradually increased until the desired effect is achieved. In general, the dosage of the crystal form A of the compound of formula (I) of the present disclosure for mammals, especially human, can be between 0.001 and 1000 mg/kg body weight/day.

The crystal form A of the compound of formula (I) of the present disclosure can be administered alone or in the form of a pharmaceutical composition. The pharmaceutical composition of the present disclosure can be formulated into various suitable dosage forms according to the route of administration. The use of one or more physiologically acceptable carriers, including excipients and adjuvants, facilitates the processing of the active compound or the crystal form thereof into formulations that can be used pharmaceutically. The appropriate form of the formulation depends on the selected route of administration, and can be manufactured according to common knowledge well known in the art.

The main advantages of the crystal form, particularly crystal form A, of the compound of formula (I) of the present disclosure include:

(1) having a preparation method that is easy to operate and suitable for industrial production;

(2) having good appearance, fluidity, compressibility, being convenient for production, detection, preparation of formulations, transportation and storage;

(3) having a high purity, less residual solvent, higher solubility, good stability, and easy quality control;

(4) having good inhibitory activity on the CDK4/6 kinase, and having good exposure and/or bioavailability in vivo; and (5) having good efficacy in vivo and in vitro, and being useful for treating and/or preventing diseases associated with CDK4/6 kinase-mediated cancers.

BRIEF DESCRIPTION OF THE DRAWINGS

The drawings described herein are used for providing a further understanding of the present disclosure and constitute a part of the present application, and exemplary examples of the present disclosure and the description thereof are used for explaining the present disclosure and do not constitute an undue limitation on the present disclosure. In the drawings.

DETAILED DESCRIPTION OF EMBODIMENTS

Figure 1:
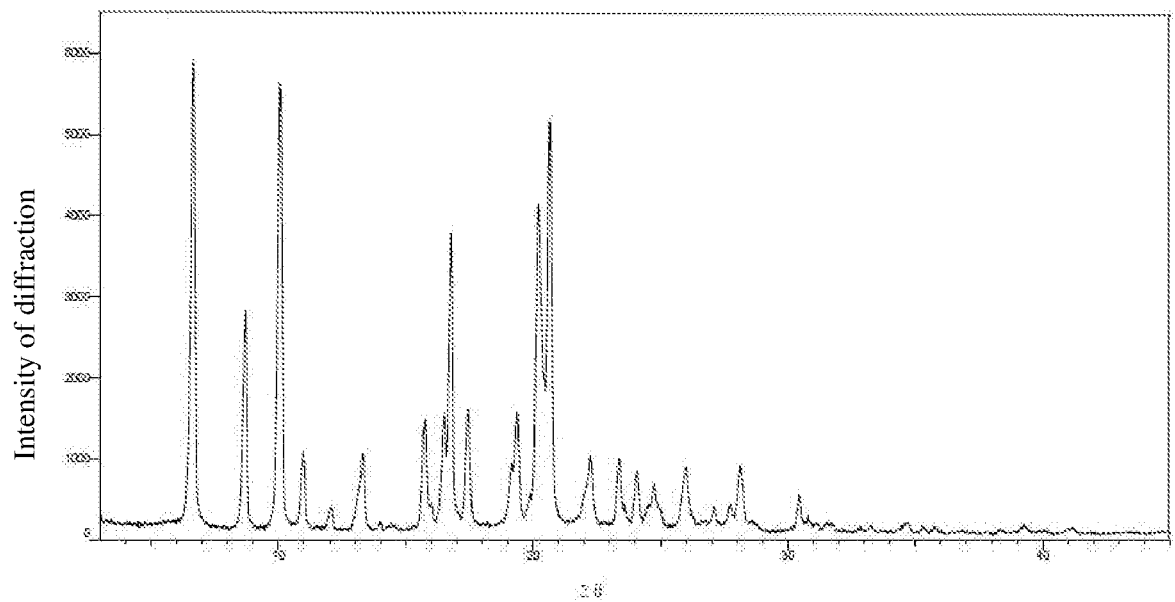
FIG. 1 is an X-ray powder diffraction (XRPD) pattern of the crystal form A of the compound of formula (I), wherein the ordinate indicates the intensity of diffraction, and the abscissa indicates the angle of diffraction (2θ).

The substantive content of the present disclosure is further illustrated below in conjunction with specific examples of the present disclosure, and it should be understood that the following examples are only used for illustrating the present disclosure, but not to limit the scope of protection of the present disclosure. In the following examples, where no specific conditions are indicated, they are carried out according to conventional conditions or the recommendations of the manufacturers. Where no manufacturers are indicated for drugs or reagents used, they are all conventional products that are commercially available.

Although many materials and operation methods used in the following examples are well known in the art, the present disclosure is still described in as much detail as possible. It would be clear to a person skilled in the art that unless otherwise specified, the materials and operation methods used in the following examples are well known in the art.

The compound of formula (I) used in the following examples or experimental examples is prepared according to the preparation method of Example 1 in the description of the patent application PCT/CN 2014/095615.

Preparation Examples

Preparation Methods for the Crystal Form A of the Compound of Formula (I)

Preparation Method I: 5.0 g of the compound of formula (I) was taken, 75 mL of acetone was added, and the compound of formula (I) was dissolved under magnetic stirring, a white solid immediately precipitates out, and after 5 h of stirring, the same was filtered with suction to obtain a white powder which was dried in a vacuum at 35° C. for 16 h to obtain a solid identified as crystal form A by means of an XRPD test.

Preparation Method II: 500 mg of the compound of formula (I) was taken, 15 mL of isopropanol was added, and the compound of formula (I) was dissolved with stirring in an oil bath at 80° C. until becoming clear (within 4.0 h), cooled naturally to room temperature (32° C.) to precipitate out a white solid, further stirred at room temperature for 12 h, cooled to 15° C., and stirred for 4.0 h and filtered with suction to obtain a solid, which was dried in a vacuum at 45° C. for 16 h, and identified as crystal form A by means of XRPD and $^1$H-NMR analysis.

Preparation Method III: 5.0 g of the compound of formula (I) was taken and put into a 100 mL three-necked flask, 75 mL of sec-butanol was added, the temperature of an oil bath was controlled to 95° C., and the same was dissolved with mechanical stirring for 0.5 h and became clear. The oil bath was then cooled to 70° C., about 25 mg of the seed crystal (the crystal form A prepared by means of Preparation Method I or II) was added, a white solid began to slowly precipitate, the oil bath was further cooled to 60° C., kept at a constant temperature for 0.5 h, cooled to 55° C., kept at a constant temperature for 0.5 h, and further cooled to about 20° C., and the same was stirred for 1.5 h, filtered with suction, and rinsed with methyl tert-butyl ether (2×10 mL) to obtain a solid, which was dried in a vacuum at 65° C. for 24 h. $^1$H-NMR detection indicates no residual solvent, and XRPD analysis indicates that the solid is the crystal form A.

Preparation Method IV:

1) Preparation of a seed crystal: 40 g of the compound of formula (I) and 300 g of n-pentanol were taken and heated to 75° C.; after about 0.5 h at a stirring paddle rotation speed of R=300 r/min, the raw material began to dissolve; and after being completely dissolved and becoming clear, the raw material was further kept at 75° C. for 0.5 h. The stirring speed was reduced to R=150 r/min, and the clear solution was rapidly cooled to 55° C. within about 0.5 h. After reaching 55° C., the stirring speed was increased to R=300 r/min, the system was further cooled to 5° C. at 9° C./h, and slowly became turbid and precipitated out a solid. After reaching 5° C., the system was kept at a constant temperature for 2 hours and filtered with suction to obtain a solid, i.e. the seed crystal.

2) Preparation method for crystal form A: 50 g of the compound of formula (I) was dispersed in 300 g of n-pentanol, heated to 85° C., completely dissolved and became clear, and was rapidly cooled to 58° C. (85-58° C./h). 0.1 g of the seed crystal mentioned above in 1) was added, the temperature was kept constant for 60 min. The system at this time slowly became turbid until a white solid appeared. The system was slowly cooled to 5° C. at a rate of 6° C./h, further kept overnight at a constant temperature, and then filtered with suction. The resulting solid was placed in a vacuum drying device and dried at 100° C. for 6 h. The resulting dried solid was dried in a vacuum at 65° C. for 24 h. $^1$H-NMR detection indicates no residual solvent, and XRPD analysis indicates that the solid is the crystal form A.

Tests on the products obtained by means of Preparation Methods I to IV indicate that the purity of the crystal form A is great then 99.7%, the content of a single maximum impurity is less than 0.08%, and almost no solvent remains.

XRPD Test

Instrument used: Bruker D2 X-ray powder diffractometer.

X-ray reflection parameters: Cu, Kα; entrance slit: 0.6 mm; divergence slit: 1 mm; scan mode: continuous; scan range: 3.0-45.0°; sampling step: 0.02°; scan time per step: 19.8 s; and detector angle: 2.0°.

The crystal form A of the compound of formula (I) is shown in an X-ray powder diffraction pattern in FIG. 1, wherein the crystal form has peaks at the following diffraction 2θ angles: 6.6±0.2°, 8.7±0.2°, 10.0±0.2°, 10.9±0.2°, 13.2±0.2°, 15.7±0.2°, 16.4±0.2°, 16.7±0.2°, 17.4±0.2°, 19.3±0.2°, 20.1±0.2°, 20.6±0.2°, 22.2±0.2°, 23.3±0.2°, 24.0±0.2°, 25.9±0.2°, 28.1±0.2°, and 30.4±0.2°.

Differential Scanning Calorimetry

The solid-state thermal properties of the crystal form A of the compound of formula (I) are studied by means of differential scanning calorimetry (DSC).

Instrument used: Q2000 differential scanning calorimeter, purchased from TA.

Measurement conditions: Purging with nitrogen at 50 ml/min, collecting data at a heating rate of 10° C./min between 25° C. and 220° C., and plotting the same with endothermic peaks downwards.

Figure 2:
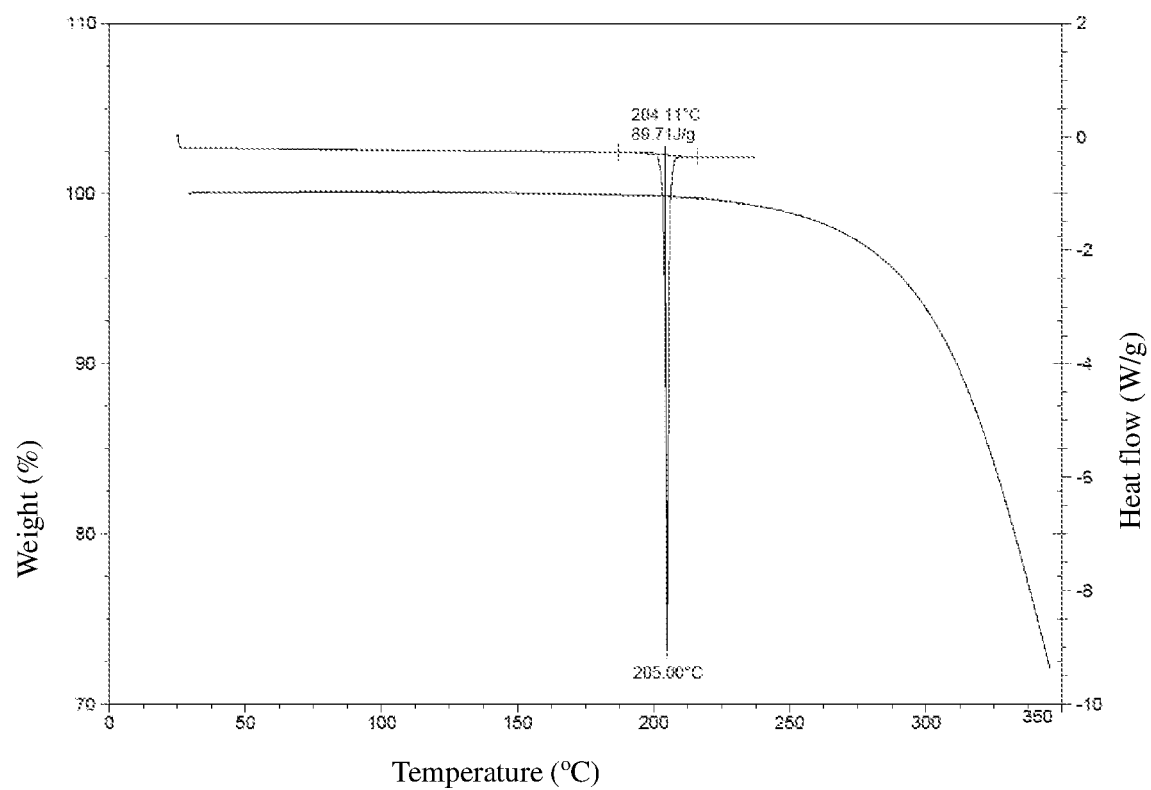
FIG. 2 is a TGA-DSC analysis diagram of the crystal form A of the compound of formula (I), wherein the ordinate on the right side indicates the weight (%), the ordinate on the left side indicates the heat flow (W/g), and the abscissa indicates the temperature T (° C.).

Measurement results: the crystal form A of the compound of formula (I) shows an endothermic peak within a range of 195° C. to 215° C., and the differential scanning calorimetry diagram is as shown in FIG. 2.

Thermogravimetric Analysis

Instrument used: Q50 thermogravimetric analyzer, purchased from TA.

Test conditions: Purging with nitrogen at 60 ml/min, and collecting data at a heating rate of 10° C./min between room temperature and 350° C.

Measurement results: The crystal form A of the compound of formula (I) has no obvious weight loss within a range of 0° C.-250° C., and the TG curve thereof is as shown in FIG. 2.

Nuclear Magnetic Analysis ($^1$H-NMR)

Instrument: Bruker Advance III 400; solvent: deuterated DMSO.

Figure 3:
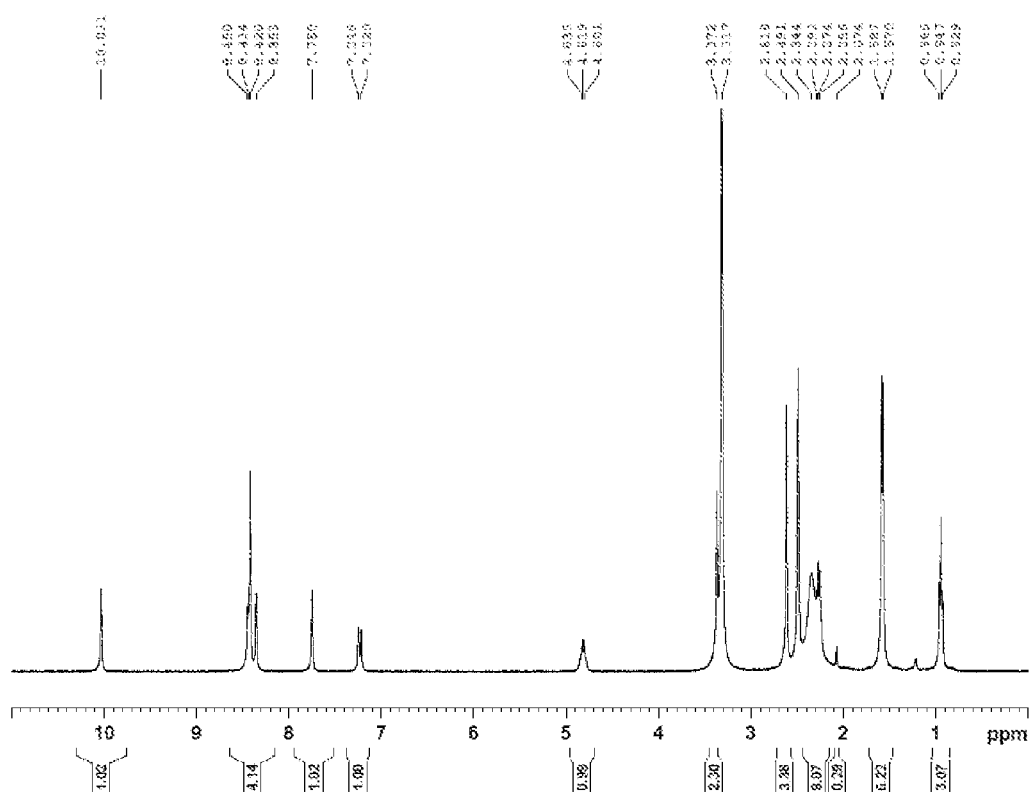
FIG. 3 is a 1H-NMR spectrum of the crystal form A of the compound of formula (I).

Measurement results: $^1$H-NMR of the crystal form A of the compound of formula (I) is as shown in FIG. 3.

Experimental Examples for Property Testing:

Experimental Example 1 Investigation of the Properties of Crystal Form A

1) Stability Test

Test product: Crystal form A of the compound of formula (I), prepared according to Preparation Method I, II, III or IV mentioned above.

Experiment Method: The test product was placed under high humidity (25° C./RH 92.5% or 40° C./RH 75%) conditions or under 60° C. conditions for 10 days, and samples were taken on the 5th and 10th days, respectively; and placed under light (4500 LX±500 LX) conditions for 10 days, a sample was taken on the 10th day and tested for related substances and XRPD, and the same was compared with the sample of day 0.

Relevant substances: Measured according to Chinese Pharmacopoeia, 2015 edition, Volume II, Appendix V D High Performance Liquid Chromatography.

XRPD measurement: Measured according to Chinese Pharmacopoeia, 2015 edition, Volume IV, 0451 X-Ray Diffraction Method.

The results of the stability experiment on the crystal form A of the compound of formula (I) are as shown in Table 1.

TABLE 1

Results of the investigation on the stability of the crystal form A of the compound of formula (I)

| Test product | Test conditions | Placement time | Appearance | Related substance (%) | XRPD |
| --- | --- | --- | --- | --- | --- |
| Crystal form A of the compound of formula (I) | 0 day | 0 day | Off-white powder | 0.11 | Crystal form A |
| | 25° C./RH 92.5% Open | 5 day | Off-white powder | 0.09 | Crystal form A |
| | | 10 day | Off-white powder | 0.09 | Crystal form A |
| | 60° C. Open | 5 day | Off-white powder | 0.11 | Crystal form A |
| | | 10 day | Off-white powder | 0.14 | Crystal form A |
| | 60° C. Closed | 5 day | Off-white powder | 0.09 | Crystal form A |
| | | 10 day | Off-white powder | 0.11 | Crystal form A |
| | 40° C./RH 75% Open | 5 day | Off-white powder | 0.10 | Crystal form A |
| | | 10 day | Off-white powder | 0.20 | Crystal form A |
| | 40° C./RH 75% Closed | 5 day | Off-white powder | 0.10 | Crystal form A |
| | | 10 day | Off-white powder | 0.20 | Crystal form A |
| | Light | 10 day | Off-white powder | 0.09 | Crystal form A |

2) Hygroscopicity Test on the Compound of Formula (I) and the Crystal Form A

Test Product:

The compound of formula (I), prepared according to the preparation method of Example 1 in the description of the patent application PCT/CN 2014/095615.

Crystal form A of the compound of formula (I), prepared according to the preparation method I, II, III or IV mentioned above.

Measurement method: Measured according to Chinese Pharmacopoeia, 2015 edition, Volume IV, General Principles, 9103 Guiding Principles for Hygroscopicity Test on Drugs.

See Table 2 for the results of the hygroscopicity experiment

TABLE 2

Hygroscopicity test results

| Test product | Moisture absorption weight gain (%) | Hygroscopicity results |
|---|---|---|
| Compound of formula (I) | 6.3 | Moisture absorbability |
| Crystal form A of the compound of formula (I) | 0.003 | No or almost no moisture absorbability |

3) Particle Size Measurement Test of Crystal Form A

Test product: Crystal form A of the compound of formula (I), prepared according to Preparation Method I, II, III or IV mentioned above.

Reagents: Tween 80 and ultrapure water.

Instrument and equipment: laser particle size analyzer, and sample disperser.

Measurement Method:

An appropriate amount of the test product was taken, 0.1 mL of a 1% Tween 80 solution was added to reduce the surface tension, and water was used as a dispersant to prepare a uniformly dispersed suspension. The same was placed in a sample dispersion device, the stirring speed was adjusted to 2000 rpm, ultrasonication was carried out for 2 min at an ultrasonic frequency of 7 KHz, and measurement was carried out.

Experiment Results:

The particle size distribution of the crystal form A of the compound of formula (I) is as follows: 10% of the sample is 2.501 μm or less, 50% is 10.432 μm or less, and 90% is 59.852 μm or less.

Experimental Example 2 Investigation of the Stability of the Compound of Formula (I) in Amorphous Form Test product: Compound of formula (I) (i.e., amorphous form), prepared according to the preparation method of Example 1 in the description of the patent application PCT/CN 2014/095615.

Experiment Method:

The test product was placed under 25° C./RH 92.5% or under 60° C. conditions for 10 days, and was sampled on the 5th and 10th days respectively; the test product was placed under light (4500 LX±500 LX) or 40° C./RH 75% conditions for 10 days, sampled on the 10th day and tested for related substances and XRPD, and compared with the sample of day 0.

Related substances: Measured according to Chinese Pharmacopoeia, 2015 edition, Volume II, Appendix V D High Performance Liquid Chromatography.

XRPD Measurement: Chinese Pharmacopoeia, 2015 edition, Volume IV, 0451 X-Ray Diffraction Method.

The results of the stability experiment on the amorphous form of the compound of formula (I) are as shown in Table 3.

TABLE 3

Results of the investigation of the stability of the amorphous form

| Test product | Test conditions | Placement time | Appearance | Related substance (%) | XRPD |
|---|---|---|---|---|---|
| Compound of formula (I) | 0 day | 0 day | Off-white powder | 0.14 | Amorphous form |
| | 25° C./RH 92.5% Open | 5 day | Off-white powder | 0.14 | Amorphous form |
| | | 10 day | Off-white powder | 0.19 | Amorphous form |
| | 60° C. Open | 5 day | Light yellow powder | 0.67 | Amorphous form |
| | | 10 day | Light yellow powder | 1.15 | Amorphous form |
| | 40° C./RH 75% Open | 10 day | Off-white powder | 0.19 | Amorphous form |
| | Light | 10 day | Light yellow powder | 10.54 | Amorphous form |

Experiment Conclusions:

After being placed under 60° C. or light conditions for 10 days, the properties, such as appearance, related substances, and XRPD, of the crystal form A had no obvious change, whereas the amorphous form had up to 10.54% of related substances under light conditions.

The results show that the crystal form A of the present disclosure exhibits good stability and low hygroscopicity characteristics, which is convenient for the production of medicaments, the preparation of formulations, transportation and storage, and is more conducive to ensuring the stability and safety of drug use. Furthermore, compared to the amorphous form, the crystal form A has good exposure and/or bioavailability in vivo, and good efficacy in vivo and in vitro.

Experimental Example 3 Investigation of the Compressibility Experiment on the Amorphous Form and the Crystal Form A of the Compound of Formula (I)

Test products: Crystal form A of the compound of formula (I), prepared according to Preparation Method I, II, III or IV mentioned above; and the amorphous form of the compound of formula (I), prepared according to the preparation method of Example 1 in the description of the patent application PCT/CN 2014/095615.

Experiment Method:

Appropriate amounts of the crystal form A and amorphous form of the compound of formula (I) were respectively taken as raw materials and separately tableted, the weight of the tablets was fixed, the thickness of the tablets (tabletting force) was adjusted, and the hardness of the tablets was measured. The change of tablet hardness with tablet thickness was investigated, and compressibility was compared.

See Table 4 for the experiment results.

TABLE 4

| Compressibility experiment results | | | | | |
|---|---|---|---|---|---|
| Tablet thickness/mm | 2.4 | 2.0 | 1.8 | 1.3 | 0.9 |
| Hardness of crystal form A/kg | 0 | 1.76 | 5.40 | 3.50 | 2.97 |
| Hardness of amorphous form/kg | 0.72 | 0.59 | 2.75 | / | / |

Note:
(1) "/" in the table means that no tablet can be formed at that tablet thickness.

(2) The smaller the tablet thickness, the greater the tabletting force.

From the experiment results in Table 4, it can be seen that at the same tablet thickness, the tablet hardness of the crystal form A is greater than that of the amorphous form. In addition, as the tablet thickness decreases (the tabletting force increases), the tablet hardness of the crystal form A can reach up to about 5.4 kg, whereas the maximum hardness of the amorphous form is about 2.75 kg; furthermore, during the process of tabletting, the amorphous form is prone to wall sticking, causing the surface of the tablet to be rough or flawed, and the amorphous form is also prone to capping, indicating that the crystal form A has better compressibility than the amorphous form, and is more conducive to the development of formulation products.

Experimental Example 4 Investigation of the Release Experiment on the Amorphous Form and Crystal Form A of the Compound of Formula (I)

Test Products: Crystal form A of the compound of formula (I), prepared according to Preparation Method I, II, III or IV mentioned above; and the amorphous form of the compound of formula (I), prepared according to the preparation method of Example 1 in the description of the patent application PCT/CN 2014/095615.

Experiment Method:

40 mg of the crystal form A and 40 mg of the amorphous form were taken and respectively added to the same types and amounts of adjuvants, the same were compressed into tablets. The disintegration and dissolution was investigated under the following conditions.

Dissolution Method: Paddle method (Chinese Pharmacopoeia, 2015 edition, Volume IV, 0931 Dissolution and Release Measurement methods, Method II); medium: 0.2% SDS aqueous solution; and rotation speed: 50 r/min.

See Tables 5 and 6 for the experiment results.

TABLE 5

| Disintegration time | | |
|---|---|---|
| Test product | Crystal form A | Amorphous form |
| Disintegration time/min | 4 | >30 min Absorbed water to become a colloid and slowly dissipated |

TABLE 6

| | Dissolution | | | | | |
|---|---|---|---|---|---|---|
| Crystal | Cumulative dissolution (%) | | | | | |
| form | 5 min | 10 min | 15 min | 30 min | 45 min | 60 min |
| Crystal form A | 69.2 | 90.7 | 93.8 | 96.6 | 97.5 | 97.9 |
| Amorphous form | 1.0 | 2.7 | 4.6 | 9.2 | 13.2 | 18.5 |

The experiment results in Tables 5 and 6 shows that the crystal form A disintegrates and dissolves faster and is completely dissolved within 60 minutes, whereas the disintegration and dissolution rates of the amorphous form are greatly reduced as compared to the crystal form A, indicating that the crystal form A is more suitable for the development of formulations.

Lastly, it should be noted that the above examples are only used for illustrating, rather than limiting, the technical solutions of the present disclosure. Although the present disclosure has been described in detail with reference to the preferred examples, a person of ordinary skill in the art should understand that modifications to the specific embodiments of the present disclosure or equivalent replacements of some of the technical features thereof can still be made without departing from the spirit of the technical solutions of the present disclosure, and they should all be included in the scope of the technical solutions claimed by the present disclosure.

What is claimed is:

1. Crystal form A of a compound of formula (I), characterized by an X-ray powder diffraction pattern comprising characteristic peaks at 6.6±0.2°, 10.0±0.2°, 13.2±0.2°, 17.4±0.2°, 20.1±0.2°, and 20.6±0.2° expressed as 2θ angles using Cu-Kα radiation, Formula (I)

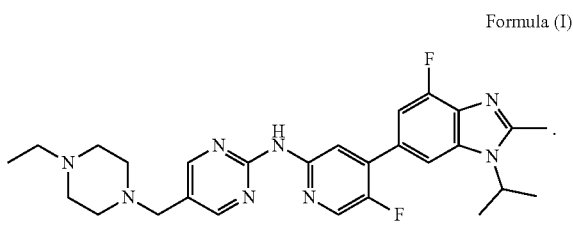 [SMILES: CCN1CCN(Cc2cnc(Nc3cc(-c4cc(F)c5nc(C)n(C(C)C)c5c4)c(F)cn3)nc2)CC1]

2. The crystal form A of claim 1, characterized by an X-ray powder diffraction pattern comprising characteristic peaks at 6.6±0.2°, 8.7±0.2°, 10.0±0.2°, 10.9±0.2°, 13.2±0.2°, 15.7±0.2°, 16.4±0.2°, 17.4±0.2°, 20.1±0.2°, 20.6±0.2°, and 30.4±0.2° expressed as 2θ angles using Cu-Kα radiation.

3. The crystal form A of claim 1, characterized by an X-ray powder diffraction pattern comprising characteristic peaks at 6.6±0.2°, 8.7±0.2°, 10.0±0.2°, 10.9±0.2°, 13.2±0.2°, 15.7±0.2°, 16.4±0.2°, 16.7±0.2°, 17.4±0.2°, 19.3±0.2°, 20.1±0.2°, 20.6±0.2°, 22.2±0.2°, 23.3±0.2°, 24.0±0.2°, 25.9±0.2°, 28.1±0.2°, and 30.4±0.2° expressed as 2θ angles using Cu-Kα radiation.

4. The crystal form A of claim 1, characterized by an X-ray powder diffraction pattern obtained using Cu-Kα radiation substantially as shown in FIG. 1.

5. The crystal form A of claim 1, characterized by a differential scanning calorimetry (DSC) diagram comprising an endothermic peak at about 195° C.-215° C.

6. The crystal form A of claim 1, characterized by a differential scanning calorimetry (DSC) diagram comprising an endothermic peak at 205±3° C.

7. The crystal form A of claim 1, characterized by a differential scanning calorimetry (DSC) diagram substantially as shown in FIG. 2.

8. A method for preparing the crystal form A of the compound of formula (I) of claim 1, comprising:
dissolving the compound of formula (I) in an organic solvent, and heating the same to 60° C.-100° C. with stirring until the compound is dissolved;
cooling to a temperature between 30° C.-55° C. to precipitate out a solid;
cooling to a temperature between 0° C.-25° C., and stirring at the temperature for 1-24 h; and
collecting the precipitated solid, and drying to obtain the crystal form A.

9. A method for preparing the crystal form A of the compound of formula (I) of claim 1, comprising:
dissolving the compound of formula (I) in an organic solvent, and heating the same to 70° C.-100° C.;
after the compound is dissolved, cooling to a temperature between 50° C.-75° C., adding a seed crystal, and keeping at the temperature to precipitate out a solid; and
cooling to 0° C.-25° C., keeping at the temperature, collecting the precipitated solid, and drying to obtain the crystal form A,
wherein the seed crystal is the crystal form A of the compound of formula (I) or a solid precipitated during the preparation of the crystal form A of the compound of formula (I), and
wherein the amount of the seed crystal added is 0.1%-3% of the mass of the compound of formula (I).

10. The method of claim 9, wherein
the organic solvent is selected from one of or any combination of two or more of the following solvents:

(1) alcohol solvents selected from fatty alcohol solvents, alicyclic alcohol solvents and aromatic alcohol solvents, wherein the fatty alcohol solvents are selected from methanol, ethanol, propanol, isopropanol, n-butanol, isobutanol, tert-butanol, sec-butanol, n-pentanol, n-hexanol, ethylene glycol, propylene glycol or glycerol; the alicyclic alcohol solvents are selected from cyclopentanol, cyclopentylmethanol, cyclohexanol, cyclohexylmethanol or cyclohexylethanol; and the aromatic alcohol solvents are selected from benzyl alcohol, phenylethanol or phenylpropanol;
(2) ketone solvents selected from fatty ketone solvents and cyclic ketone solvents, wherein the fatty ketone solvents are selected from methyl ethyl ketone, methyl isopropyl ketone, acetone, methyl butanone or methyl isobutyl ketone; and the cyclic ketone solvents are selected from cyclopropanone, cyclohexanone, isophorone or N-methylpyrrolidone;
(3) nitrile solvents selected from acetonitrile or propionitrile;
(4) ether solvents selected from fatty ether solvents and cyclic ether solvents, wherein the fatty ether solvents are selected from diethyl ether, dipropyl ether, diisopropyl ether, methyl tert-butyl ether, ethyl butyl ether, ethyl tert-butyl ether, dibutyl ether or dipentyl ether, and the cyclic ether solvents are selected from ethylene oxide, 1,2-propylene oxide, tetrahydrofuran, 2-methylfuran, dioxolane or 1,4-dioxane;
(5) amide solvents selected from formamide, N,N-dimethylformamide, N,N-dimethylacetamide, N,N-dimethylpropionamide or N,N-diethylpropionamide; and
(6) sulfoxide solvents selected from dimethyl sulfoxide, diethyl sulfoxide or benzyl phenyl sulfoxide.

11. A pharmaceutical composition comprising the crystal form A of the compound of formula (I) of claim 1, and optionally one or more pharmaceutical carriers and/or diluents.

12. The pharmaceutical composition of claim 11, wherein the pharmaceutical composition further comprises one or more additional anti-tumor agents and/or immunosuppressive agents selected from one or more of methotrexate, capecitabine, gemcitabine, doxifluridine, pemetrexed disodium, pazopanib, imatinib, erlotinib, lapatinib, gefitinib, vandetanib, trastuzumab, bevacizumab, rituximab, trastuzumab, paclitaxel, vinorelbine, docetaxel, doxorubicin, hydroxycamptothecin, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, nitrogen mustard, melphalan, chlorambucil, carboplatin, cisplatin, oxaliplatin, lobaplatin, topotecan, camptothecin, hycamtin, everolimus, sirolimus, temsirolimus, 6-mercaptopurine, 6-thioguanine, azathioprine, mycin D, daunorubicin, amycin, mitoxantrone, plicamycin and aminoglutethimide.

13. A method for treating a disease associated with CDK4/6 kinase-mediated cancers in a mammal in need thereof, comprising administering to the mammal in need thereof a therapeutically effective amount of the crystal form A of the compound of formula (I) of claim 1.

14. The method of claim 13, wherein the disease associated with CDK4/6 kinase-mediated cancers is selected from brain tumor, lung cancer, squamous cell carcinoma, bladder cancer, stomach cancer, ovarian cancer, peritoneal cancer, pancreatic cancer, breast cancer, head and neck cancer, cervical cancer, endometrial cancer, rectal cancer, liver cancer, kidney cancer, esophageal adenocarcinoma, esophageal squamous cell carcinoma, prostatic cancer, female reproductive tract cancer, carcinoma in situ, lymphoma, neurofibromatosis, thyroid cancer, bone cancer, skin cancer, brain cancer, colon cancer, testicular cancer, gastrointestinal stromal tumor, prostate tumor, mast cell tumor, multiple myeloma, melanoma, glioma, and sarcoma.

15. The method of claim 8, wherein
the organic solvent is selected from one of or any combination of two or more of the following solvents:
(1) alcohol solvents selected from fatty alcohol solvents, alicyclic alcohol solvents and aromatic alcohol solvents, wherein the fatty alcohol solvents are selected from methanol, ethanol, propanol, isopropanol, n-butanol, isobutanol, tert-butanol, sec-butanol, n-pentanol, n-hexanol, ethylene glycol, propylene glycol or glycerol; the alicyclic alcohol solvents are selected from cyclopentanol, cyclopentylmethanol, cyclohexanol, cyclohexylmethanol or cyclohexylethanol; and the aromatic alcohol solvents are selected from benzyl alcohol, phenylethanol or phenylpropanol;
(2) ketone solvents selected from fatty ketone solvents and cyclic ketone solvents, wherein the fatty ketone solvents are selected from methyl ethyl ketone, methyl isopropyl ketone, acetone, methyl butanone or methyl isobutyl ketone; and the cyclic ketone solvents are selected from cyclopropanone, cyclohexanone, isophorone or N-methylpyrrolidone;
(3) nitrile solvents selected from acetonitrile or propionitrile;
(4) ether solvents selected from fatty ether solvents and cyclic ether solvents, wherein the fatty ether solvents are selected from diethyl ether, dipropyl ether, diisopropyl ether, methyl tert-butyl ether, ethyl butyl ether, ethyl tert-butyl ether, dibutyl ether or dipentyl ether, and the cyclic ether solvents are selected from ethylene oxide, 1,2-propylene oxide, tetrahydrofuran, 2-methylfuran, dioxolane or 1,4-dioxane;
(5) amide solvents selected from formamide, N,N-dimethylformamide, N,N-dimethylacetamide, N,N-dimethylpropionamide or N,N-diethylpropionamide; and
(6) sulfoxide solvents selected from dimethyl sulfoxide, diethyl sulfoxide or benzyl phenyl sulfoxide.

16. A method for preparing the crystal form A of the compound of formula (I) of claim 1, comprising:
dissolving the compound of formula (I) in an organic solvent to form a mixture, heating the mixture to a temperature between 60° C.-100° C. and stirring until the compound is dissolved, further stirring and cooling resultant solution to a temperature between 0° C.-25° C. to precipitate out a solid, keeping at the temperature and stirring for 1-24 h, filtering with suction, and drying to obtain the crystal form A.

17. The method of claim 16, wherein
the organic solvent is selected from one of or any combination of two or more of the following solvents:
(1) alcohol solvents selected from fatty alcohol solvents, alicyclic alcohol solvents and aromatic alcohol solvents, wherein the fatty alcohol solvents are selected from methanol, ethanol, propanol, isopropanol, n-butanol, isobutanol, tert-butanol, sec-butanol, n-pentanol, n-hexanol, ethylene glycol, propylene glycol or glycerol; the alicyclic alcohol solvents are selected from cyclopentanol, cyclopentylmethanol, cyclohexanol, cyclohexylmethanol or cyclohexylethanol; and the aromatic alcohol solvents are selected from benzyl alcohol, phenylethanol or phenylpropanol;
(2) ketone solvents selected from fatty ketone solvents and cyclic ketone solvents, wherein the fatty ketone solvents are selected from methyl ethyl ketone, methyl isopropyl ketone, acetone, methyl butanone or methyl isobutyl ketone; and the cyclic ketone solvents are selected from cyclopropanone, cyclohexanone, isophorone or N-methylpyrrolidone;
(3) nitrile solvents selected from acetonitrile or propionitrile;
(4) ether solvents selected from fatty ether solvents and cyclic ether solvents, wherein the fatty ether solvents are selected from diethyl ether, dipropyl ether, diisopropyl ether, methyl tert-butyl ether, ethyl butyl ether, ethyl tert-butyl ether, dibutyl ether or dipentyl ether, and the cyclic ether solvents are selected from ethylene oxide, 1,2-propylene oxide, tetrahydrofuran, 2-methylfuran, dioxolane or 1,4-dioxane;
(5) amide solvents selected from formamide, N,N-dimethylformamide, N,N-dimethylacetamide, N,N-dimethylpropionamide or N,N-diethylpropionamide; and
(6) sulfoxide solvents selected from dimethyl sulfoxide, diethyl sulfoxide or benzyl phenyl sulfoxide.

18. The method of claim 16, wherein the organic solvent is selected from acetone, isopropanol, butanol and n-pentanol.

19. The method of claim 8, wherein the organic solvent is selected from acetone, isopropanol, butanol and n-pentanol.

20. The method of claim 9, wherein the organic solvent is selected from acetone, isopropanol, butanol and n-pentanol.

* * * * *